US012678170B2

(12) United States Patent
    Whelan

(10) Patent No.: US 12,678,170 B2
(45) Date of Patent: Jul. 14, 2026

(54) TOURNIQUET CLIP AND TOURNIQUET

(71) Applicant: NOBLE HOUSE GROUP PTY. LTD.,
    Kingston (AU)

(72) Inventor: Chris Whelan, Newhall, CA (US)

(73) Assignee: NOBLE HOUSE GROUP PTY. LTD.
    (AU)

( * ) Notice: Subject to any disclaimer, the term of this
    patent is extended or adjusted under 35
    U.S.C. 154(b) by 73 days.

(21) Appl. No.: 18/288,390

(22) PCT Filed: May 2, 2022

(86) PCT No.: PCT/AU2022/050404
    § 371 (c)(1),
    (2) Date: Oct. 26, 2023

(87) PCT Pub. No.: WO2022/226604
    PCT Pub. Date: Nov. 3, 2022

(65) Prior Publication Data
    US 2024/0206884 A1      Jun. 27, 2024

(30) Foreign Application Priority Data
    Apr. 30, 2021    (AU) ................................. 2021901271

(51) Int. Cl.
    *A61B 17/132* (2006.01)
    *A44B 11/06* (2006.01)
(52) U.S. Cl.
    CPC ........ *A61B 17/1327* (2013.01); *A44B 11/065* (2013.01)
(58) Field of Classification Search
    CPC ............ A61B 17/1327; A61B 17/1322; A61B 17/132; A61B 17/1325; A44B 11/065; A44B 11/006; A44B 11/005; A44B 11/2553; A44B 18/0088; A44B 11/06; A44B 19/303; A63B 21/4009; A63B 21/4011; A63B 21/4017; A41D 13/0568; A41D 13/055; A61H 2201/165; A61H 39/04; A61H 2011/005; A61H 11/00
    See application file for complete search history.

(56) References Cited

U.S. PATENT DOCUMENTS

| | | | |
|---|---|---|---|
| 3,800,450 A | 4/1974 | Laugherty | |
| 4,314,568 A | 2/1982 | Loving | |
| 8,608,036 B2 * | 12/2013 | Mori ......................... | A45F 3/14 |
| | | | 224/267 |
| 10,039,553 B2 | 8/2018 | Van Sparrentak et al. | |
| 10,945,741 B2 | 3/2021 | Green et al. | |

(Continued)

FOREIGN PATENT DOCUMENTS

| | | |
|---|---|---|
| CN | 202589599 | 12/2012 |
| CN | 103637828 | 3/2014 |

(Continued)

*Primary Examiner* — Tan-Uyen T Ho
*Assistant Examiner* — Bridget E. Rabaglia
(74) *Attorney, Agent, or Firm* — Galbreath Law Offices, P.C.; John A. Galbreath

(57) ABSTRACT

A joiner for a tourniquet, such as a tourniquet clip. (20) has first and second portions (22a, 22b) each portion connected, mounted or adapted to connect to or mount on a tourniquet strap or strap assembly (12), the first and second portions (22a, 22b) joined, directly or indirectly, by at least one frangible portion (24).

20 Claims, 9 Drawing Sheets

(56)                   References Cited

U.S. PATENT DOCUMENTS

| 11,759,213 | B2 | 9/2023 | Whelan | |
|---|---|---|---|---|
| 2002/0103450 | A1 | 8/2002 | Corrales | |
| 2008/0312682 | A1 | 12/2008 | Shams | |
| 2009/0043168 | A1 | 2/2009 | Parambil | |
| 2013/0312160 | A1* | 11/2013 | Spencer | A41F 1/002 |
| | | | | 2/244 |
| 2017/0079665 | A1 | 3/2017 | Fellowes | |
| 2021/0093326 | A1 | 4/2021 | Jones | |

FOREIGN PATENT DOCUMENTS

| GB | 2453465 | | 4/2009 | |
|---|---|---|---|---|
| GB | 2542412 | A * | 3/2017 | A61B 17/1322 |

* cited by examiner

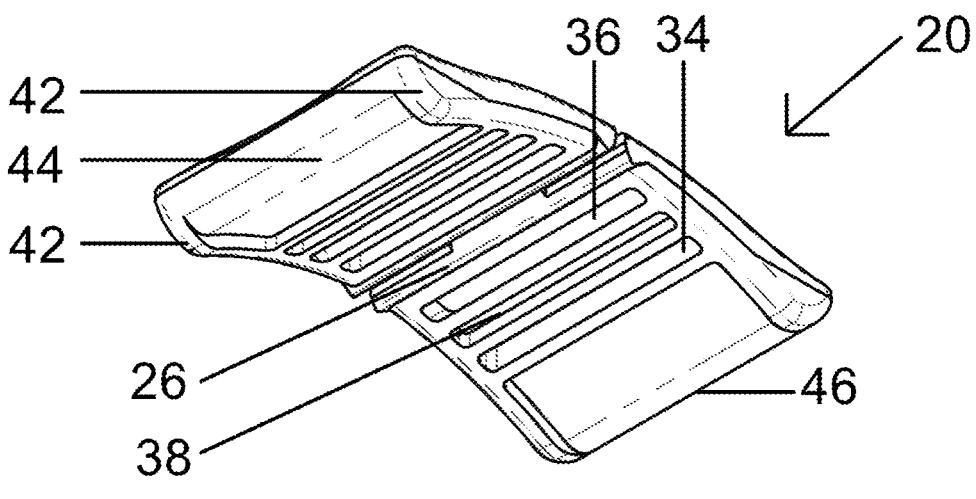
Figure 2
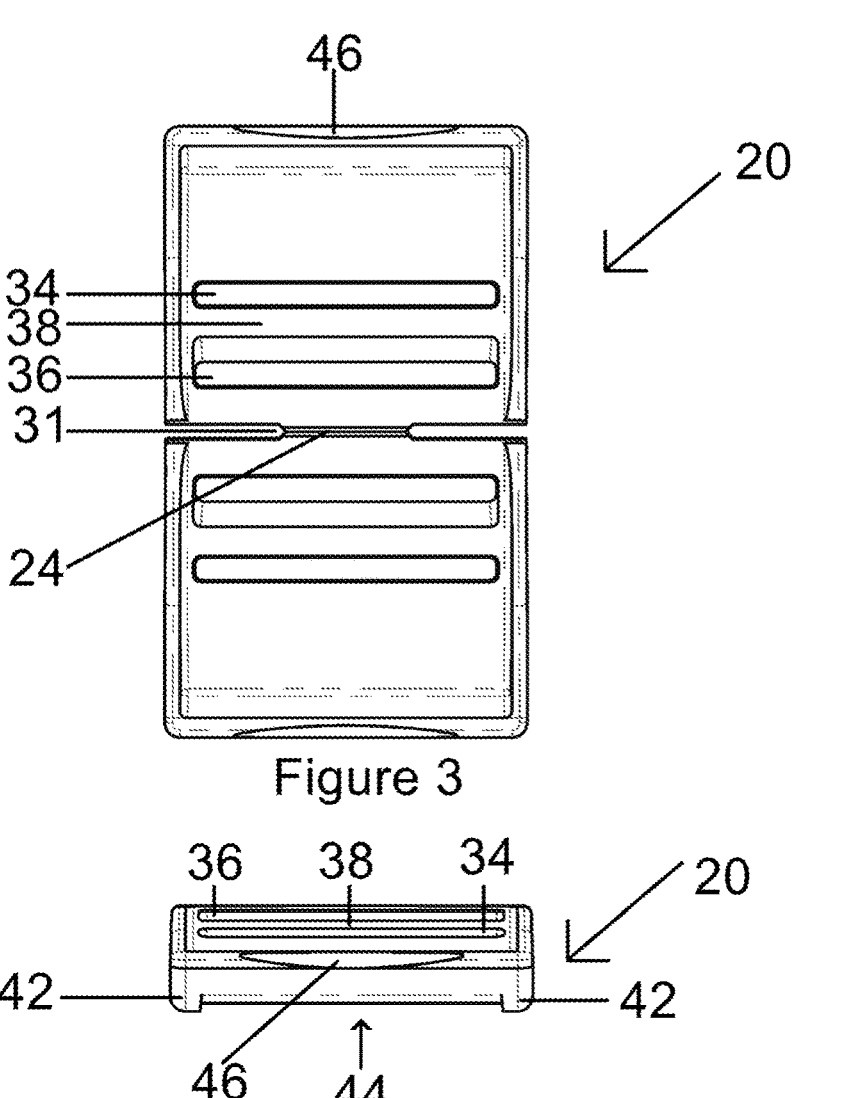
Figure 3
Figure 5

TOURNIQUET CLIP AND TOURNIQUET

FIELD OF INVENTION

This invention relates to tourniquets and more particularly to tourniquet Clips

BACKGROUND

Tourniquets are used to apply pressure to a limb to reduce blood flow. A common use is to make it easier for a medical practitioner to insert a cannula into a vein of a patient, whether to take a blood sample or for introduction of fluids into the patient.

A common tourniquet comprises a length of elastic material with complementary clips, typically a male and a female clip, mounted toward the opposite end of the elastic material. One or both of the clips may be movable along the length of elastic material. The tourniquet may be applied open, wherein the male and female clips are disengaged, or it may be looped over the patient's arm in the closed configuration, wherein the male and female clips are engaged to form a closed loop. The elastic material is positioned around the patient's limb, typically an arm. One or both of the clips are moved along the length to tighten the tourniquet. After use the clips are disconnected allowing removal of the tourniquet. An example of such a tourniquet is disclosed in PCT/AU2018/051180. There is nothing to stop reuse of the tourniquet. Further, such devices require at least three separate components—the length of elastic material and two separate clips.

SUMMARY OF THE INVENTION

In one broad form the invention provides a joiner for a tourniquet, the joiner having first and second portions each portion connected, mounted or adapted to connect to or mount on a tourniquet strap or tourniquet strap assembly, the first and second portions joined, directly or indirectly, by at least one frangible portion.

The joiner may be all or part of a tourniquet clip and/or may be part of a tourniquet strap assembly.

As used in the description and claims the term "tourniquet strap" is to be interpreted as including a strap that is comprised of more than one components or pieces and is not limited to a single length of tourniquet strap.

In another broad form the invention provides a tourniquet clip having first and second portions adapted to connect to a tourniquet strap, so as to form a closed loop, the first and second portions joined, directly or indirectly, by at least one frangible portion.

In another broad form the invention provides a tourniquet comprising a tourniquet strap with a tourniquet clip having first and second portions connected to the strap so as to from a closed loop, the first and second portions joined, directly or indirectly, by at least one frangible portion.

Where the joiner is part of a tourniquet strap assembly the tourniquet strap may comprise at least two lengths each joined to a different one of the first and second portions.

Accordingly, in another broad form the invention provides the tourniquet strap assembly comprising at least two lengths of tourniquet strap and a joiner having first and second portions joined, directly or indirectly, by at least one frangible portion, each portion joined, directly or indirectly, to a different length.

In another broad form the invention provides a tourniquet comprising a tourniquet strap and a tourniquet clip having first and second portions connected to or mounted on the strap at different positions on the tourniquet strap, so as to form a closed loop, the tourniquet strap comprising at least two lengths joined, directly or indirectly, by a joiner having first and second portions joined, directly or indirectly, by at least one frangible portion, each portion joined, directly or indirectly, to a separate length.

Where the at least one frangible portion is part of a tourniquet strap assembly such an assembly may be used with any tourniquet clip and the tourniquet clip need not have a frangible portion to provide the single use feature. Thus, conventional, existing tourniquet clips, such as that of PCT/AU2018/051180 may be used with such a tourniquet strap assembly.

Preferably the clip is formed unitarily but may be formed of two or more separate components that are joined together. Where the clip is comprised of two or more components, preferably the components are joined together in a manner that prevents an end user separating the components or parts of one or more components, other than via the at least one frangible portion.

As used throughout the description and claims the term "formed unitarily", and any variation of this term, is to be understood to mean that the object so described is a single object, as opposed to parts that are formed separately and then assembled together.

Preferably at least one of the portions is movable along the tourniquet strap so as to change the effective size of the loop. One or both of the portions may be connected to the strap at a fixed location.

Preferably the two portions are connected at a generally central location by the at least one frangible portion, so that when the frangible portion is broken there are two parts. However, there may be more than one location for the at least one frangible portion. The clip may include a central portion with the first portion connected to the central portion by at least one first frangible portion and the second portion connected to the central portion by at least one second frangible portion. Where there is a single frangible portion the frangible portion need not be located centrally.

A frangible portion may be formed of a single frangible part or multiple frangible parts.

A frangible portion is preferably elongate.

At least one frangible portion may extend between two parts of the clip and the two parts are rotatable about the at least one frangible portion to engage each other at at least one location spaced from the at least one frangible portion, whereby application of increasing force to urge the two parts to rotate about the at least one location places the at least one frangible portion in tension and to break.

The at least one location may comprise an elongate engagement surface(s) or line(s) and/or one or more engagement points spaced along a path. The two parts may be configured so that different amounts of rotation about the at least one frangible portion are required before the two parts engage each other at different locations along the engagement surface(s) or line(s) and/or engage each other at different engagement points.

The at least one frangible portion may extend between two parts of the clip, with the two parts having each having at least one opposed face defining at least one groove therebetween. The at least one groove may be V-shaped.

The opposed faces may define at least one elongate groove with a constant cross section along its length. Alternatively the at least one groove may vary across the width of the clip. The at least one groove may define an included angle. The included angle defined at one location may be different to the included angle at another location.

The joiner may have a first direction with the first and second portions spaced apart in the first direction.

Preferably at least one frangible portion extends along at least one line or path sideways/transversely (preferably generally perpendicularly but not necessarily) to the first direction. There may be one line or path or multiple lines or paths. Where there are multiple frangible portions two or more of the frangible portions may be spaced apart from each other along the first direction (e.g. lengthways). Where there are multiple frangible portions two or more of the frangible portions may be spaced apart from each other transversely to the first direction (e.g. sideways).

The joiner may have at least one first location on one side of a line or path and at least one second location on another side of a line or path, said first and second locations adapted to be pushed together, pulled apart or rotated by a user to break the at least one frangible portion extending along the respective line or path. A plane extending through a first and a second location preferably passes to one side of a line or path. The plane may pass through said a line or path. Where at least one frangible portion is broken by application of tension to the at least one frangible portion, location of first and second locations in a plane offset to the at least one frangible portion allows a simple pushing or pulling action to more easily break the at least one frangible portion.

BRIEF DESCRIPTION OF THE DRAWINGS

FIG. 2 is a perspective view from below of the tourniquet clip of FIG. 1.

FIG. 3 is a plan view from above of the tourniquet clip of FIG. 1.

FIG. 5 is an end view of the tourniquet clip of FIG. 1.

DETAILED DESCRIPTION OF PREFERRED AND OTHER EMBODIMENTS

Figure 6:
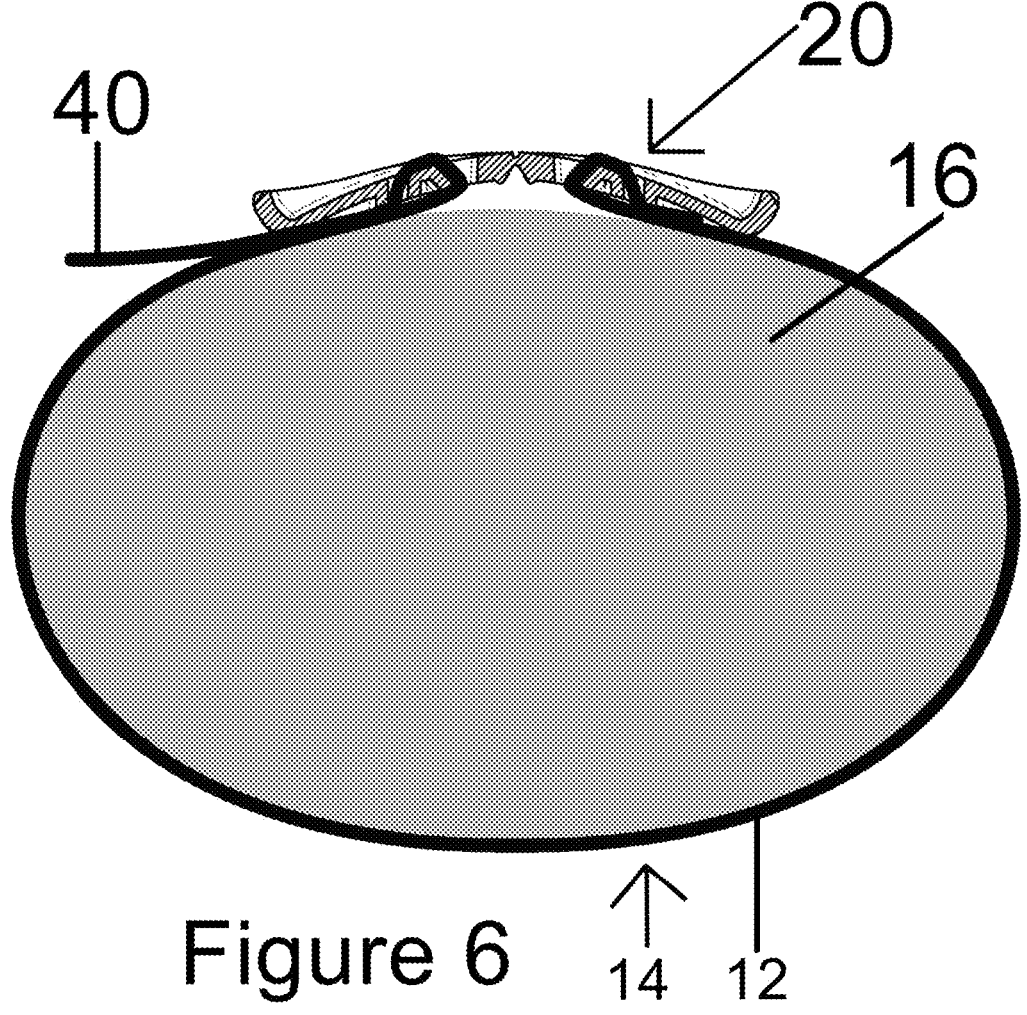
FIG. 6 is schematic cross sectional view of a tourniquet on a patent's arm and tensions for use.
Figure 7:
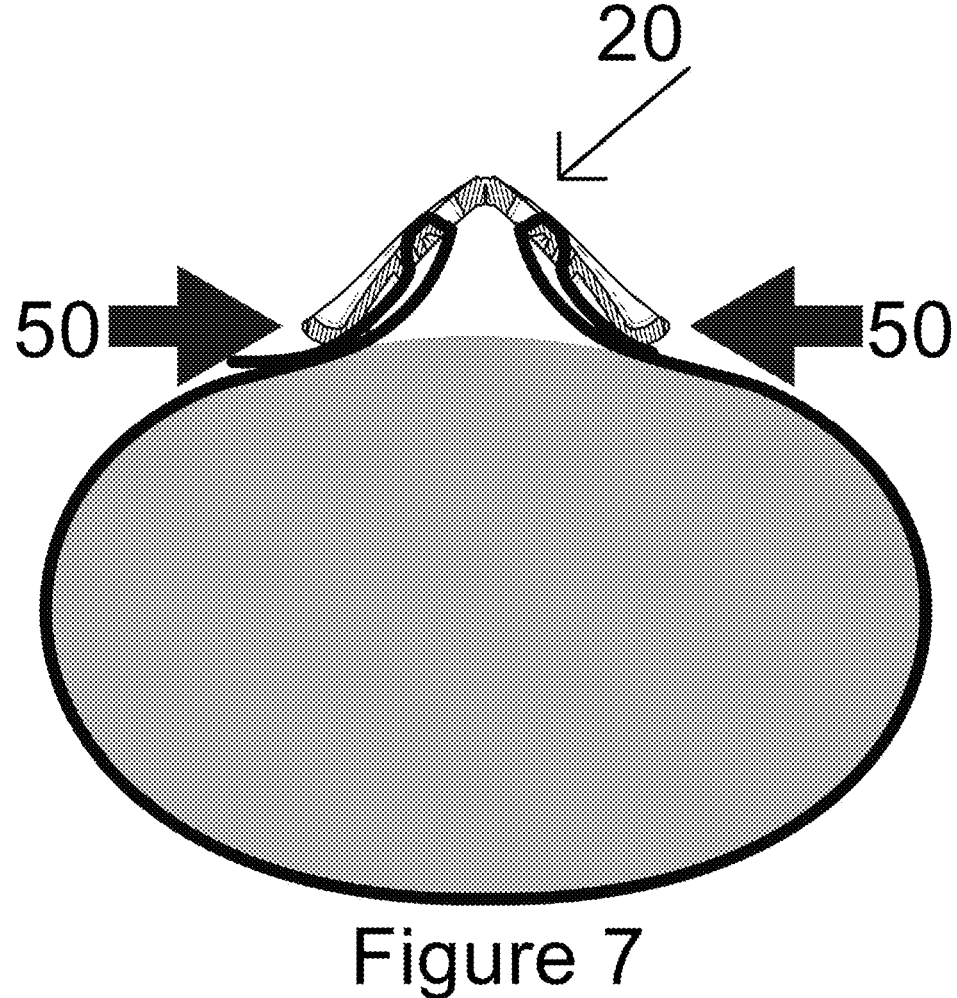
FIG. 7 is schematic cross sectional view of the arrangement of FIG. 6 as the clip is being compressed during removal.
Figure 8:
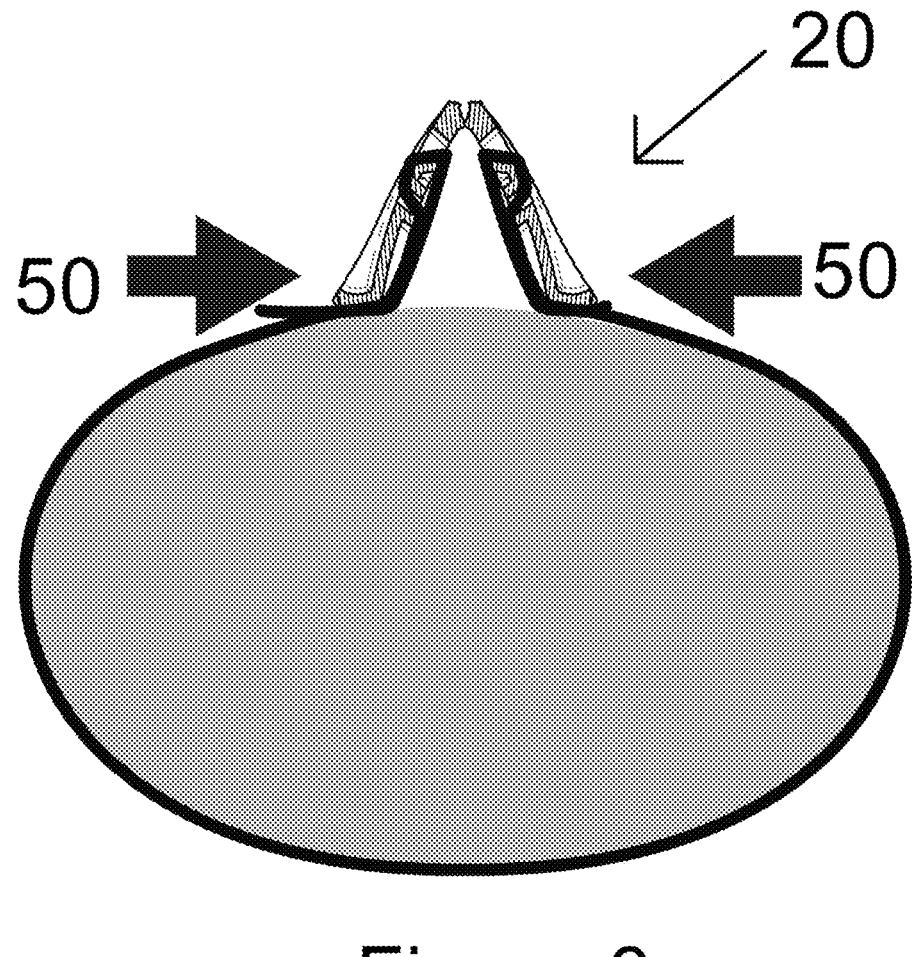
FIG. 8 is schematic cross sectional view of the arrangement of FIG. 6 as the clip is being broken.

Referring to FIGS. 1 to 5 there is shown a tourniquet clip 20 according to a first embodiment of the invention, for use with a tourniquet strap 12 to form a tourniquet 14 that may be placed about a body part 16, as shown in FIGS. 6 to 8.

The clip 20 comprises two substantially identical portions 22a and 22b that are joined together by a frangible bridge 24. The two portions 22a and 22b need not be identical.

Figure 4:
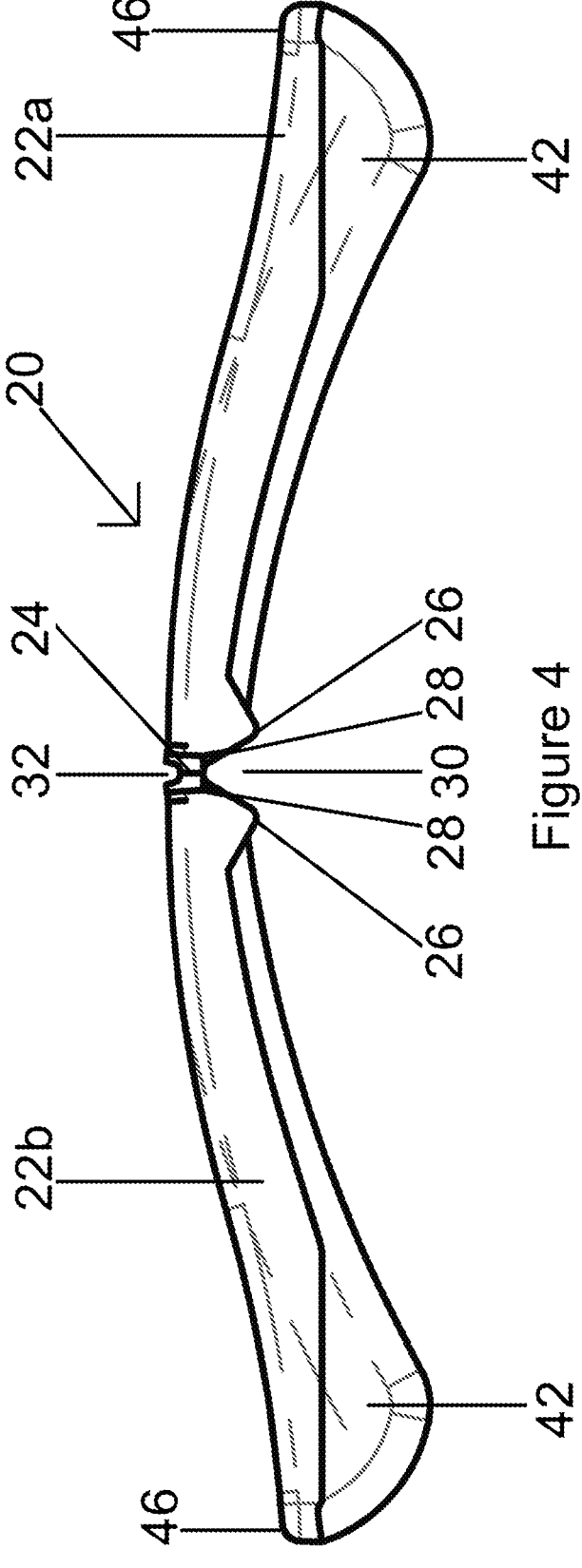
FIG. 4 is a side view of the tourniquet clip of FIG. 1.

As best seen in FIG. 4, the bridge 24 joining the two portions 22a, 22b is relatively thin and is located away from the bottom edge region 26 of the two portions. In the 'normal' configuration the two portions 22a, 22b have opposing faces 28 that extend from the bridge to the bottom edge region 26 in a divergent manner. The faces 28 thus define a generally V-shaped groove 30. Preferably there is a small groove 32 above the bridge 24. In the embodiment shown the bridge 24 is about 8 mm wide and extends across about one third of the width of the clip 20, as best seen in FIG. 3. The bridge 24 has a vertical thickness of about 0.6 mm. The upper groove 32 is about 0.6 mm wide and about 0.6 mm deep. In the embodiment shown the included angle of the V-shaped groove 30 is about 60 degrees but may range from about 45 degrees to about 90 degrees.

Whilst the embodiment shown has a single bridge at the central location, there could be two or more bridges extending sideways, separated from each other by slots or gaps.

Each of the portions 22a, 22b is provided with structure to allow each to connect to the tourniquet strap 12. In this implementation the structure comprises two spaced apart slots 34 and 36 that define a bar 38 therebetween. Each end of the tourniquet strap 12 may be passed through the slot 34 from underneath, around bar 38 and downwards through slot 36, as best seen in FIGS. 6 to 8. Adjustment of the effective size of the tourniquet loop is made by changing the position of the tourniquet strap 12 relative to one or both parts, such as by pulling on a free end 40 of the tourniquet strap 12. The exact arrangement of the connection of the tourniquet strap 12 to the clip 20 is not critical to the invention and other methods of connection and adjustment may be used. For example, one end of the tourniquet strap 12 may be fixed relative to the clip. The clip may be formed integrally around one end of the tourniquet strap 12, so avoiding the need for the adjustment structure (34, 36 and 38) in one part.

The sides of the clip are provided with downwardly extending edge portions 42, as best seen in FIG. 4 and these edge portions 42 provide a slot 44 into which the strap 12 is located and also rest against the patient's skin, so that in use the strap is not tightly sandwiched between the clip and the patient's skin. Whilst preferred, this is not an essential feature of the invention.

In use, the tourniquet 20 is placed on the patient and tightened, as shown in FIG. 6. The medical procedure is carried out and the medical practitioner then removes the tourniquet by pushing the ends 46 of the clip together, as indicated by arrows 50 in FIG. 7. The clip is configured so as to be generally curved, so that the centre portion including bridge 28 lies above the free ends 46 of portions 22a and 22b. This inwards force causes the two portions 22a and 22b to bend about bridge 24, with the centre moving upwards away from the patent's skin.

The two portions 22a and 22b bend about bridge 24 until faces 28 contact each other. Continued inwards force on the two portions 22a and 22b urges pivoting about lower edge region 26, placing tension on the bridge 24. As the bridge 24 is narrower and thinner than the portions 22a, and 22b increased force will cause the bridge to break, as indicated in FIG. 8. Because the centre portion has moved away from the patient's skin, when the bridge breaks the now free inner ends of the two portions will move away from the patient's skin, so avoiding the broken ends digging into the patient. The bending of the two portions 22a and 22b about bridge 24 also tends to bend the bridge 24 and depending on the material used the bridge 24 may break merely due to this bending action and before faces 28 contact each other.

The loop is now broken and the tourniquet 20 may be easily removed from the patient's arm. Breaking of the bridge 24 renders the tourniquet 20 incapable of reuse.

The angle of the V-shaped groove, the number of bridges across the clip and the distance from the bridge(s) 24 to the lower edge region 26 depend on the material used.

In the embodiment shown the faces 28 extend below the general lower surface of the clip and so the lower edge region 26 defines two protruding ridges that extend transversely across the clip 20. Depending on the material used they may be omitted or the faces 28 may be so short so as to create a groove rather than a ridge extending below the general lower surface of the clip at that location.

Figure 9:
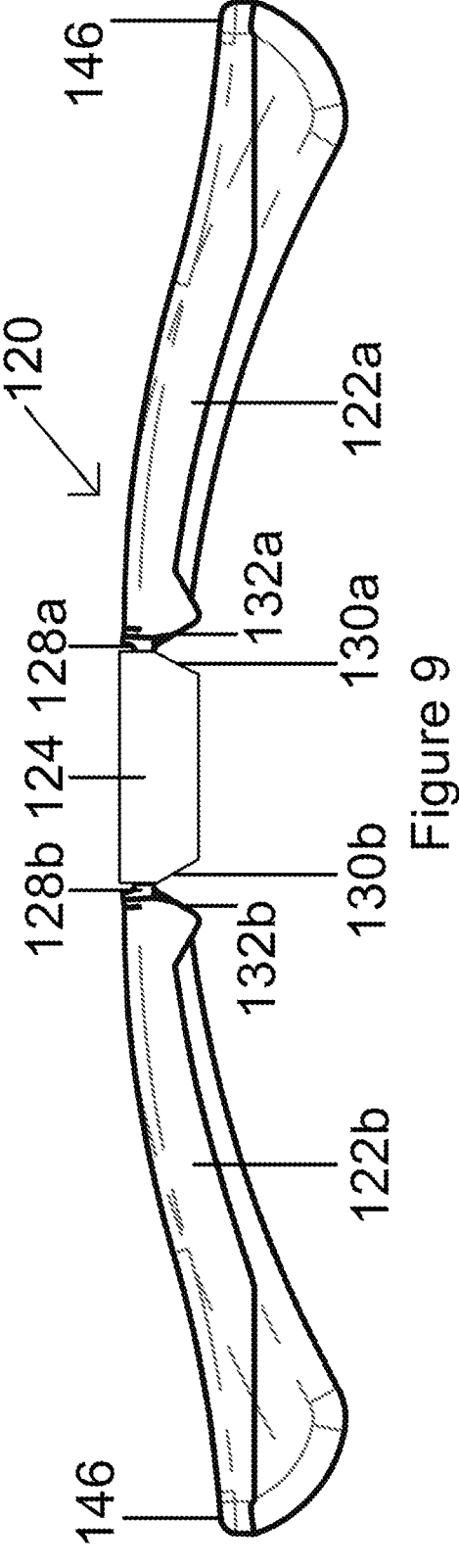
FIG. 9 is a view of a tourniquet clip according to another embodiment of the invention.

FIG. 9 shows a clip 120 according to a variation of the invention. The clip 120 has two portions 122*a* and 122*b* that are substantially the same as portions 22*a* and 22*b* of the first embodiment. In this embodiment a central portion 124 is located between portions 122*a* and 122*b*. Portions 122*a* and 122*b* are joined to central portion by frangible bridges 128*a* and 128*b*. The central portion 124 has angled faces 130*a* and 130*b* that oppose angled faces 132*a* and 132*b* on portions 122*a* and 122*b* respectively. One or both of portions 122*a* and 122*b* may be detached from the central portion 124 using the technique described for the first embodiment by pushing ends 146 together. It will be appreciated that only one of the frangible bridges 128*a* and 128*b* is required to allow separation of the clip into two or more parts. As such one of the frangible bridges 128*a* and 128*b* may be omitted. Again, the bending of the either of the two portions 122*a* and 122*b* relative to the central portion 124 also tends to bend the respective bridge 128*a* or 128*b* and depending on the material used the respective bridge 128*a* or 128*b* may break merely due to this bending action and before respective faces 130 and 132*a* or 130*b* and 132*b* contact each other.

Figure 10:
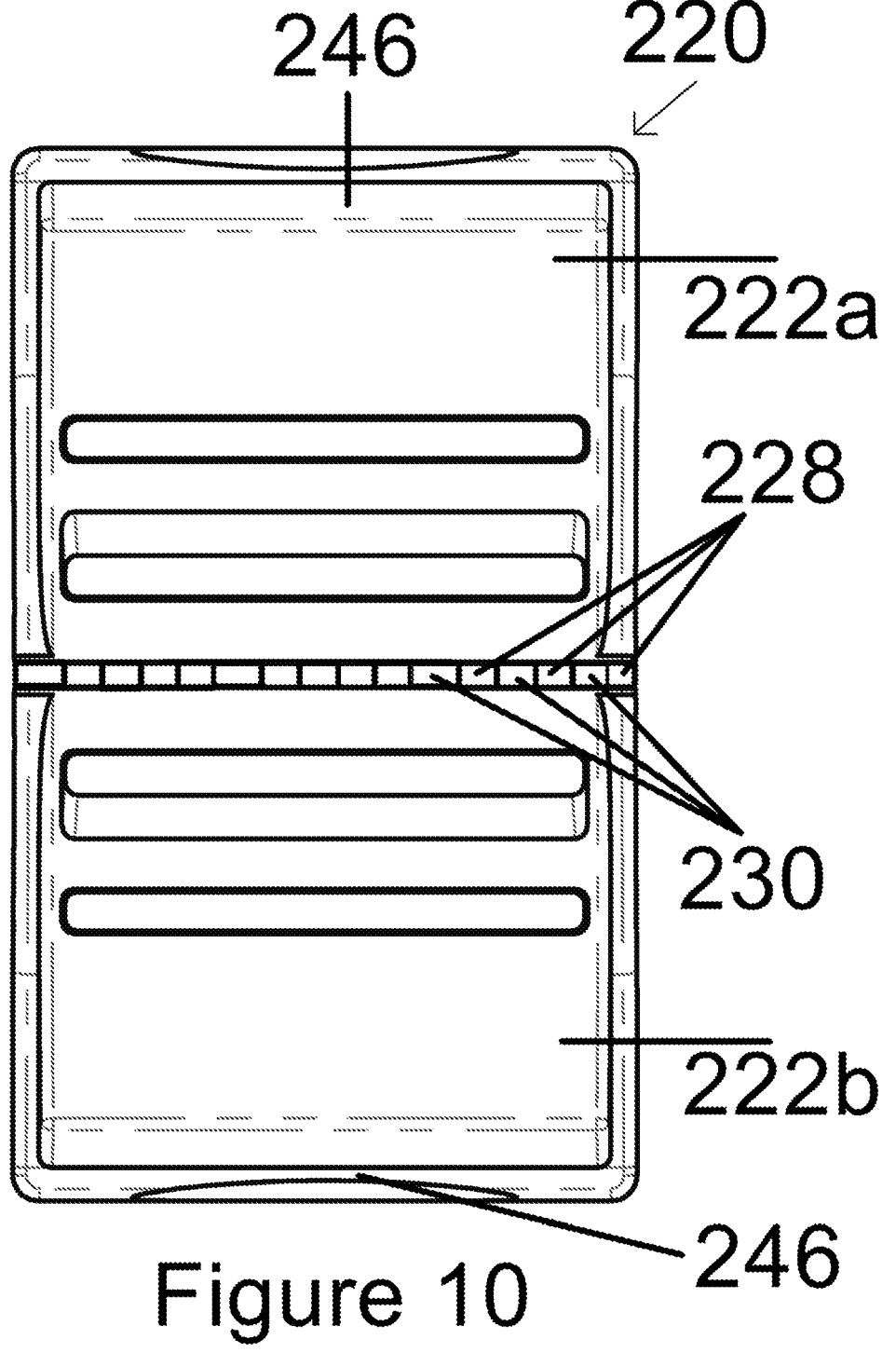
FIG. 10 is a plan view from above of a tourniquet clip according to another embodiment of the invention.

FIG. 10 shows a third embodiment 220, which is substantially the same as the first embodiment, except for the frangible bridge arrangement. In this embodiment the clip 220 has portions 222*a* and 222*b* joined by a multitude of small bridges 228 that extends across the width of the clip with apertures 230 between adjacent bridges 228. Bridges 228 are broken by pushing ends 146 together and causing portions 222*a* and 222*b* to bend bridges 228. The bridges may break merely due to this bending action or may break when angled faces (not shown) corresponding to faces 28 or the first embodiment contact each other and the ends 146 are pushed further together.

The use of multiple small bridges allows breakage of one bridge at a time, similar to tearing along a perforated line, rather than needing to break a single large bridge. The use of multiple bridges is not limited to the third embodiment and may be applied to any embodiment of the invention.

The embodiments shown have a groove that has the same dimensions across the width of the clip, so when the clip is bent the opposing faces contact each other across the width substantially simultaneously. To aid breaking of the bridge (s) the angle of the groove(s) may change across the width of the clip. Thus, as the clip is bent the portion of the opposing faces at narrower portion(s) of the groove will contact each other before the portion of the opposing faces at wider portion(s) of the groove. This will cause more tension to be applied to the bridge(s) at the narrower portion(s), so causing breakage to occur at the narrower portion(s) first. Thus, for example, the groove may have a smaller included angle at one end and the included angle may progressively increase across the width of the clip, so causing the bridge(s) to break at the end with the smaller included angle first. Alternatively the included angle in the centre of the clip may be less than at its edges, so promoting breaking in the centre first. Other methods of generating differential tension in the bridge(s) may be used.

Rather than using an angled groove the two parts may be provided with one or more complementary engagement points, lines and/or surfaces that engage each other after different amounts of movement or rotation about the bridge(s). Thus, for example, protrusions of different lengths may be provided on one or both parts that engage. An elongate protrusion or wall rather than a series of protrusions may be provided on one or both of the two parts, with the wall(s) providing an engagement surface or surfaces that engage at different points after different amounts of movement To aid breakage of the bridge(s), the ends of the bridge(s) may be formed with an inwards direct V, indicated by numeral 31 in FIG. 3. Where a frangible portion comprises multiple bridges an inwards directed V may be applied to one or more of the individual bridges.

Figure 11:
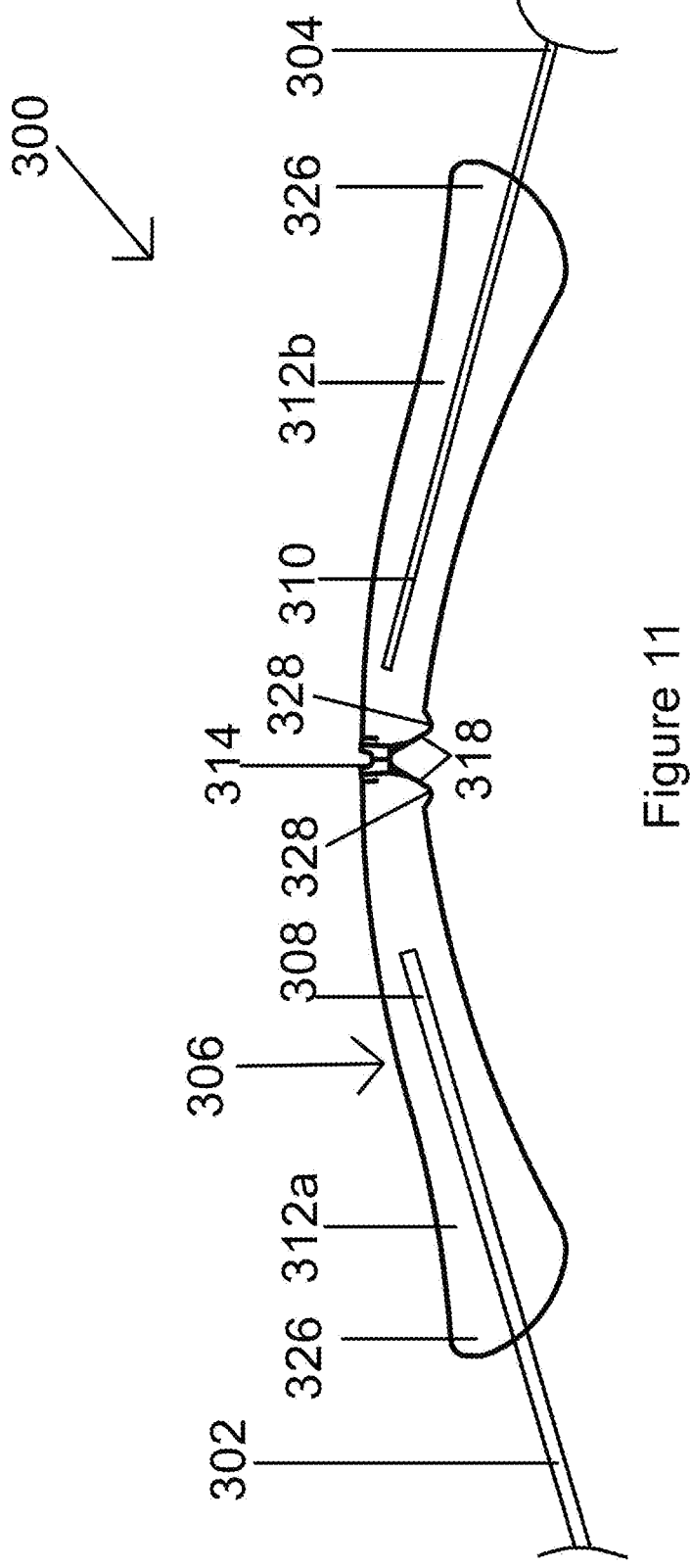
FIG. 11 is schematic cross sectional view of a tourniquet strap with a frangible section according to another embodiment of the invention.

FIG. 11 shows a tourniquet strap 300 according to another embodiment of the invention. The tourniquet strap 300 may be used with the tourniquet clip of the other embodiments or may be used with existing/conventional tourniquet clips, such as that of PCT/AU2018/051180.

The tourniquet strap 300 comprises two lengths 302 and 304 of strap material, typically an elastic strap material. The ends of the lengths 302 and 304 (not shown), may be connected to a single use tourniquet clip, such as the two portions 22*a* and 22*b* of the embodiment of FIG. 1, or two separate parts of a conventional, existing tourniquet clip, such as that of PCT/AU2018/051180. The nature of the tourniquet clip itself or how it is attached to the tourniquet strap 300 is not relevant and any clip and method or attachment may be used.

The lengths 302 and 304 are joined together by joiner 306. In this embodiment the joiner 306 is formed unitarily. Preferably the joiner 306 and is formed about the ends 308, 310 of the two lengths 304, 306, most preferably by a plastics injection moulding process. This avoids further assembly but the joiner may be formed separately from the lengths 304, 306. The joiner may also be made of separate components that are assembled after manufacture.

In terms of frangibility the joiner 306 is functionally the same as the clip 20 of the first embodiment, with substantially identical portions 312*a* and 312*b* joined together by a frangible bridge 314. The two portions 312*a* and 312*b* need not be identical. The two portions 312*a* and 312*b* have opposing faces 318 that extend from the bridge to the bottom edge region in a divergent manner. The faces 318 thus define a generally V-shaped groove 322. In a similar manner to the first embodiment the joiner may be broken by pushing the ends 326 of the joiner together.

This inwards force causes the two portions 312*a* and 312*b* to bend about bridge 314, with the bridge 314 moving upwards away from the patent's skin.

The two portions 312*a* and 312*b* bend about bridge 314 until faces 318 contact each other. Continued inwards force on the two portions 312*a* and 312*b* urges pivoting about lower edge region 328, placing tension on the bridge 314. As the bridge 314 is narrower and thinner than the portions 312*a* and 312*b* increased force will cause the bridge to break. As with the other embodiments, the bending of the two portions 312*a* and 312*b* about bridge 314 also tends to bend the bridge 314 and depending on the material used the bridge 314 may break merely due to this bending action and before faces 318 contact each other.

Figure 1:
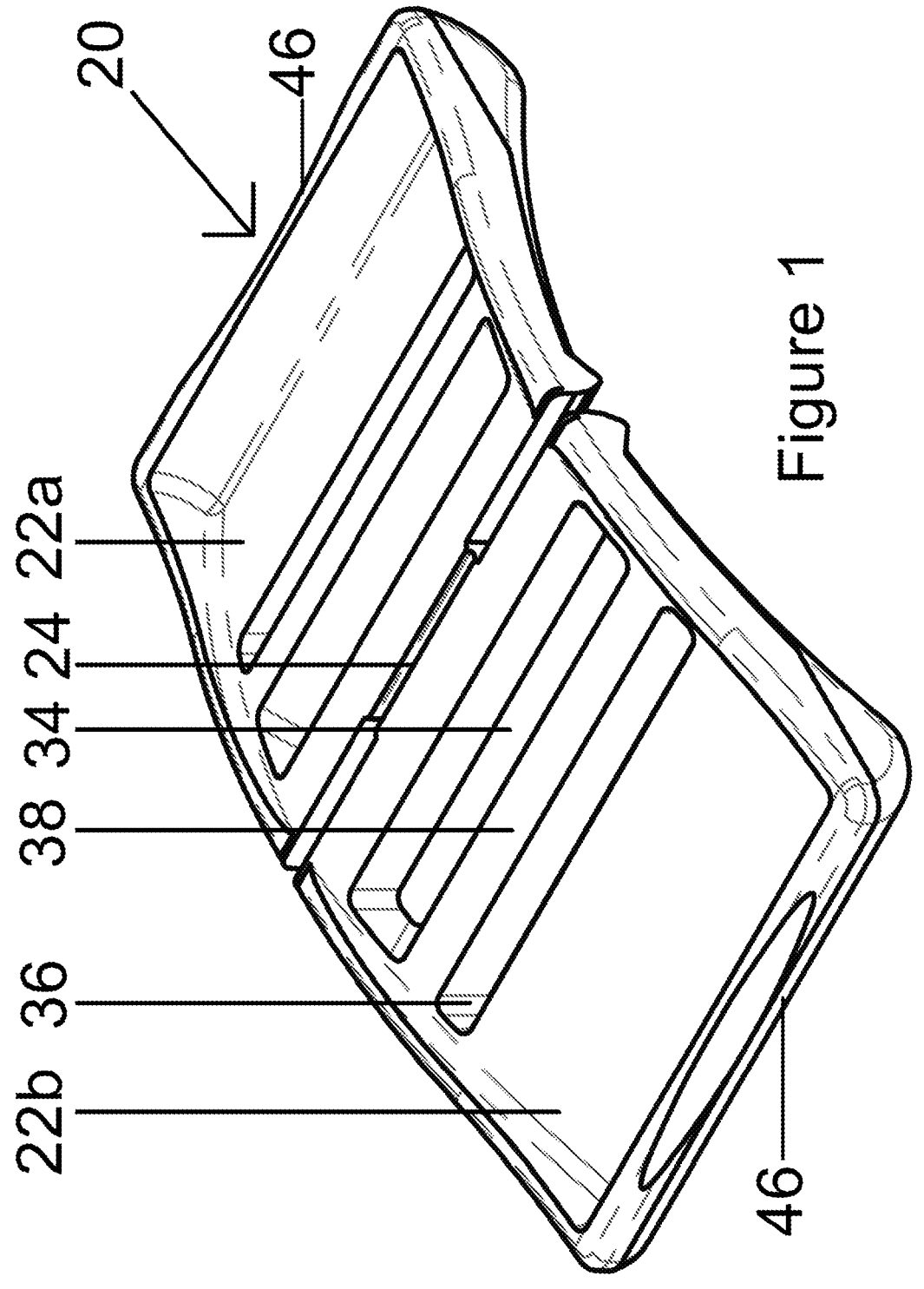
FIG. 1 is a perspective view from above of a tourniquet clip according to one implementation of the invention.

Whilst the joiner has only been described with reference to a version similar to the embodiment of FIG. 1, it will be appreciated that all of the features described or claimed in relation to the other embodiments of the invention may be applied to a joiner of the invention.

It will be appreciated that one or both two portions 312*a* and 312*b* may be formed substantially the same as portions 22*a* and 22*b* of the first embodiment and the respective length 304 or 306 mounted for movement relative to the joiner.

Where one or both of lengths 304 or 306 is mounted for movement relative to the joiner a clip with or without adjustment may be used. Where a clip without adjustment is used its two parts it may be mounted on the ends of the two lengths.

Whilst the invention has been described with reference to embodiments that require movement, and more particularly bending or rotation, about a line or axis that is generally parallel to a line defined by the at least one frangible portion, the invention is not limited to that arrangement. Bending or rotation about a line or axis generally perpendicular, or at any other angle, to a line defined by the at least one frangible portion is within the scope of the invention.

Whilst bending or pivoting is the preferred method of breaking (such as by generating tension) the at least one frangible portion the invention is not limited to that method and other means, such as a sliding action between two parts, may be used break (whether by the generating tension or shearing forces or otherwise) in the at least one frangible portion.

Whilst in the preferred implementations of the invention the joiner or clip is formed unitarily, such as by plastics injection moulding, implementations of the invention may be formed of two or more separate components that are joined together.

Where the joiner or clip is comprised of two or more components, preferably the components are joined together in a manner that prevents an end user separating (or easily separating) two or more components or parts of one or more components, other than via breakage of at least one frangible portion. One or more of the separate components may have at least one frangible portion, whereby the respective component separates into two parts.

In the embodiments shown the ends 46, 146, 246 and 326 are located below the respective bridge or bridges and pushing the ends together causes movement of the ends (whether by bending and/or rotation about a frangible portion or otherwise) of the respective parts toward the tourniquet strap and/or limb. The invention is not limited to pushing of ends together and/or rotation of the respective parts toward the tourniquet strap and/or limb. The invention includes pulling the ends apart and also includes movement the ends away from the tourniquet strap and/or limb (i.e. 'upwards'). Where 'upwards' movement (including bending or rotation) occurs, a joiner or clip of the invention may be configured with structures similar to the groove 30 and faces 28 of the first embodiment facing upwards rather than downwards.

Whilst movement (including bending or rotation) of the parts about a line or path of the at least one frangible portion is preferred to break the respective frangible portion (whether by bending and/or generating tension), this is not essential and use of movement or forces other than by bending and/or rotation may be utilised.

Whilst bending and/or application of tension to the frangible portion(s) is the preferred method of breaking the frangible portion(s) this is not essential and application of shearing forces to break the frangible portion(s) may be utilised.

Use of movement or forces generally parallel to a line or path of at least one frangible portion may be utilised. Such movement or forces may be used to cause rotation or shearing actions.

Movement or forces may be utilised to urge rotation about an axis generally perpendicular to the line or path of at least one frangible portion, so as to break the at least one frangible portion from one end of the line or path.

Unless the context clearly requires otherwise, it is to be understood that, if any prior art is referred to herein, such reference does not constitute an admission that the prior art forms a part of the common general knowledge in the art, in Australia or any other country.

Unless the context clearly requires otherwise, throughout the description and any claims the words "comprise", "comprising", and the like are to be construed in an inclusive sense as opposed to an exclusive or exhaustive sense; that is to say, in the sense of "including, but not limited to".

The features of the invention described or mentioned in this document may be combined in any combination of features where features are not mutually exclusive.

It will be apparent to those skilled in the art that many obvious modifications and variations may be made to the embodiments described herein without departing from the spirit or scope of the invention.

The claims defining the invention are as follows:

1. A tourniquet clip having first and second portions, each of the first and second portions connected, mounted or adapted to connect to or mount on a tourniquet strap at different positions on the tourniquet strap, so as to form a closed loop when so connected or mounted, the first and second portions joined, directly or indirectly, by at least one bendable frangible portion, said at least one bendable frangible portion intended to be broken by a user;

the at least one bendable frangible portion extends in a first direction from a first section to a second section of the tourniquet clip;

the first and second sections are rotatable relative to each other about a line extending transverse to the first direction by bending the bendable frangible portion from a rest position, at which the at least one bendable frangible portion is not bent, in a first rotational direction toward a second position at which first parts of the first and second sections are:

a) closer to each other than at the rest position or b) engage each other and prevent further rotation in the first direction;

wherein movement of the first and second sections from the rest position in the first rotational direction:

I. to or toward the second position breaks the at least one bendable frangible portion, or II. to the second position and application of additional force urging the first and second sections to move in the first rotational direction breaks the at least one bendable frangible portion.

2. The tourniquet clip of claim 1 wherein the first and second portions are joined, directly or indirectly to each other by the at least one bendable frangible portion, so that when the at least one bendable frangible portion is broken there are at least two parts.

3. The tourniquet clip of 1 wherein the rotation between the rest and second positions is up to about 90 degrees.

4. The tourniquet clip of claim 3 wherein the rotation between the rest and second positions is between about 45 and about 90 degrees.

5. The tourniquet clip of claim 1 wherein movement, or application of increasing force to move the first and second sections relative each other, places the respective at least one bendable frangible portion in tension.

6. The tourniquet clip of claim 5 wherein the first parts of the first and second sections engage each other at at least one location spaced from the at least one bendable frangible portion.

7. The tourniquet clip of claim 6 wherein the at least one location comprises an elongate engagement surface or line and/or one or more engagement points spaced along a path.

8. The tourniquet clip of claim 7 wherein the first and second sections each have at least one opposed face extending transversely to the first direction defining a part of at least one groove that extends in an elongate direction transverse to the first direction therebetween;

the at least one bendable frangible portion extends between the at least one opposed faces, and at least part of an opposed face of the respective first and second sections comprises the first part of the respective section.

9. The tourniquet clip of claim 8 wherein the first and second portions are connected at more than one location by the at least one bendable frangible portion.

10. The tourniquet clip of claim 9 comprising at least a central portion, and the central portion comprises the first section and the first and second portions comprise second sections with the first portion connected to the central portion by at least one first frangible portion and the second portion connected to the central portion by at least one second frangible portion.

11. The tourniquet clip of claim 8 wherein the at least one elongate groove has a constant cross section transverse to the elongate direction.

12. The tourniquet clip of claim 8 wherein the at least one groove has a cross section transverse to the elongate direction that varies along the elongate direction.

13. The tourniquet clip of claim 8 wherein the at least one groove defines an included angle.

14. The tourniquet clip of claim 13 wherein the included angle is up to about 90 degrees.

15. The tourniquet clip of claim 14 wherein the included angle is between about 45 and about 90 degrees.

16. The tourniquet clip of claim 13 wherein the included angle defined at one position along the elongate direction of the at least one groove is different to the included angle at another position along the elongate direction of the at least one groove.

17. The tourniquet clip of claim 8 wherein the tourniquet clip is formed unitarily.

18. A tourniquet comprising a single length of tourniquet strap and a unitarily formed tourniquet clip as claimed in claim 17, said first and second portions mounted on the tourniquet strap at different positions so as to form a closed loop, and both of the first and second portions are movable along the tourniquet strap so as to change the effective size of the loop.

19. A tourniquet comprising at least one length of tourniquet strap and a tourniquet clip as claimed in claim 1 connected to or mounted on at least one of the at least one length of the strap.

20. The tourniquet of claim 19 wherein the tourniquet strap and the tourniquet clip form a closed loop.

* * * * *